United States Patent
Chmelevskii Petrovich et al.

(10) Patent No.: US 12,354,268 B2
(45) Date of Patent: Jul. 8, 2025

(54) METHOD FOR AUTOMATIC SEGMENTATION OF CORONARY SINUS

(71) Applicant: XSPLINE S.P.A., Bolzano (IT)

(72) Inventors: Mikhail Chmelevskii Petrovich, Bolzano (IT); Aleksandr Sinitca, Bolzano (IT); Anastasiia Fadeeva, Bolzano (IT); Werner Rainer, Bolzano (IT)

(73) Assignee: XSPLINE S.P.A., Bolzano (IT)

( * ) Notice: Subject to any disclaimer, the term of this patent is extended or adjusted under 35 U.S.C. 154(b) by 488 days.

(21) Appl. No.: 17/846,311

(22) Filed: Jun. 22, 2022

(65) Prior Publication Data

US 2022/0414882 A1    Dec. 29, 2022

(30) Foreign Application Priority Data

Jun. 23, 2021    (IT) .................. 102021000016502

(51) Int. Cl.
*A61B 6/50*    (2024.01)
*A61B 6/00*    (2006.01)
(Continued)

(52) U.S. Cl.
CPC ............ *G06T 7/0014* (2013.01); *A61B 6/503* (2013.01); *A61B 6/5223* (2013.01); *G06T 7/11* (2017.01);
(Continued)

(58) Field of Classification Search
CPC ....... G06T 2200/08; G06T 2207/30048; G06T 2207/30101; G06T 7/0014; G06T 7/11;
(Continued)

(56) References Cited

U.S. PATENT DOCUMENTS 6,842,638 B1 *   1/2005   Suri .................... G06T 7/64
                                                        600/431
9,968,257 B1 *   5/2018   Burt .................... A61B 5/0035
(Continued)

OTHER PUBLICATIONS

Baskaran Id Lohendran et al: "Automatic segmentation of multiple cardiovascular structures from cardiac computed tomography angiography images using deep learning Icahn School of Medicine at Mount Sinai, Mount Sinai Heart", May 6, 2020 (May 6, 2020), XP055896253, Retrieved from the Internet: URL:https://journals.plos.org/plosone/article/file?id=I0.1371/journal.pone.0232573&type=printable [retrieved on Mar. 1, 2022] * p. 2-p. 5 *.
(Continued)

*Primary Examiner* — Andrew M Moyer
*Assistant Examiner* — Ahmed A Nasher
(74) *Attorney, Agent, or Firm* — Leason Ellis LLP

(57) ABSTRACT

Method, executed by a computer, for identifying a coronary sinus of a patient, comprising: receiving a 3D image of a body region of the patient; extracting 2D axial images of the 3D image taken along respective axial planes, 2D sagittal images of the 3D image taken along respective sagittal planes, and 2D coronal images of the 3D image taken along respective coronal planes; applying an axial neural network to each 2D axial image to generate a respective 2D axial probability map, a sagittal neural network to each 2D sagittal image to generate a respective 2D sagittal probability map, and a coronal neural network to each 2D coronal image to generate a respective 2D coronal probability map; generating, based on the 2D probability maps, a 3D mask of the coronary sinus of the patient.

17 Claims, 6 Drawing Sheets

(51) Int. Cl.
*G06T 7/00* (2017.01)
*G06T 7/11* (2017.01)
*G06V 10/25* (2022.01)
*G06V 10/32* (2022.01)
*G06V 10/44* (2022.01)
*G06V 10/774* (2022.01)
*G06V 10/82* (2022.01)
*A61B 6/03* (2006.01)

(52) U.S. Cl.
CPC ............ *G06V 10/25* (2022.01); *G06V 10/32* (2022.01); *G06V 10/44* (2022.01); *G06V 10/774* (2022.01); *G06V 10/82* (2022.01); *A61B 6/032* (2013.01); *G06T 2200/04* (2013.01); *G06T 2200/08* (2013.01); *G06T 2207/10081* (2013.01); *G06T 2207/20076* (2013.01); *G06T 2207/20081* (2013.01); *G06T 2207/20084* (2013.01); *G06T 2207/30048* (2013.01); *G06T 2207/30101* (2013.01); *G06V 2201/031* (2022.01)

(58) Field of Classification Search
CPC ....... G06T 2200/04; G06T 2207/10081; G06T 2207/20076; G06T 2207/20081; G06T 2207/20084; A61B 6/5223; A61B 2576/023; A61B 6/503; A61B 6/032; G06V 10/25; G06V 10/32; G06V 10/44; G06V 10/774; G06V 10/82; G06V 2201/031
See application file for complete search history.

(56) References Cited

U.S. PATENT DOCUMENTS

| | | |
|---|---|---|
| 2015/0245771 A1* | 9/2015 | Wang ............... A61B 5/725 600/407 |
| 2018/0061058 A1 | 3/2018 | Xu et al. |
| 2020/0085504 A1* | 3/2020 | Schwartz ............ A61B 5/7253 |
| 2020/0320751 A1* | 10/2020 | Siemionow ............... G06T 7/11 |
| 2021/0110533 A1* | 4/2021 | Viti ........................ G06N 3/045 |

OTHER PUBLICATIONS

Fantazzini Alice et al: "3D Automatic Segmentation of Aortic Computed Tomography Angiography Combining Multi-View 2D Convolutional Neural Networks", Cardiovascular Engineering and Technology, Springer International Publishing, Cham, vol. 11, No. 5, Aug. 11, 2020 (Aug. 11, 2020), pp. 576-586, XP037253898, ISSN: 1869-408X, DOI: 10.1007/S13239-020-00481-Z [retrieved on Aug. 11, 2020] * p. 577-p. 580 ** p. 585 *.

Cui Hejie et al: "Pulmonary Vessel Segmentation Based on Orthogonal Fused U-Net++ of Chest CT Images", Oct. 10, 2019 (Oct. 10, 2019), Computer Vision—ECCV 2020 : 16th European Conference, Glasgow, UK, Aug. 23-28, 2020 : Proceedings; [Lecture Notes in Computer Science; Issn 0302-9743], Springer International Publishing, Cham, pp. 293-300, XP047522316, ISBN: 978-3-030-58594-5 [retrieved on Oct. 10, 2019] * sections 1 and 2 *.

Italian Search Report and Written Opinion in IT Application No. 202100016502, mailed Mar. 10, 2022 (13 pages) (an English translation attached).

* cited by examiner

METHOD FOR AUTOMATIC SEGMENTATION OF CORONARY SINUS

CROSS-REFERENCE TO RELATED APPLICATIONS

This patent application claims priority from Italian patent application no. 102021000016502 filed on Jun. 23, 2021, the entire disclosure of which is incorporated herein by reference.

TECHNICAL FIELD OF THE INVENTION

The present invention relates to a method for automatic segmentation of coronary sinus, in particular by neural networks. Moreover, the present invention relates to a computer for executing said method, and to a related computer program product. In particular, the method generates a 3D mask of a coronary sinus of the patient based on a 3D image acquired through a CT apparatus.

STATE OF THE ART

As known, medical image segmentation has an essential role in computer-aided diagnosis systems in different applications. The vast investment and development of medical imaging mo-dalities such as microscopy, dermoscopy, X-ray, ultrasound, computed tomography (CT), magnetic resonance imaging (MRI), and positron emission tomography attract researchers to implement new medical image-processing algorithms. Image segmentation is considered the most essential medical imaging process as it extracts the region of interest (ROI) through a semi-automatic or automatic process. It divides an image into areas based on a specified description, such as segmenting body organs/tissues in the medical applications for border detection, tumor detection/segmentation, and mass detection.

Currently, segmentation of medical images is performed manually, semi-automatically, or automatically. Nevertheless, manual and semi-automatic segmentation is generally very time-demanding: in the case of segmentation of coronary sinus, the manual segmentation performed by an experienced cardiologist can take approximately 1 hour. Also, human factor is involved in manual segmentation and thus the results could lack accuracy and reproducibility.

Moreover, for complex anatomical structures such as the coronary sinus, known algorithms do not work because the structure of the coronary sinus varies significantly from patient to patient, and this variation cannot be determined via generally known algorithms.

SUBJECT AND SUMMARY OF THE INVENTION

According to the present invention, a method for automatic segmentation of coronary sinus by neural networks, a computer for executing said method, and a related computer program product are provided, as defined in the annexed claims.

BRIEF DESCRIPTION OF THE DRAWINGS

For a better understanding of the present invention, preferred embodiments thereof are now described, purely by way of non-limiting example and with reference to the attached drawings, wherein.

DETAILED DESCRIPTION OF PREFERRED EMBODIMENTS OF THE INVENTION

Figure 1:
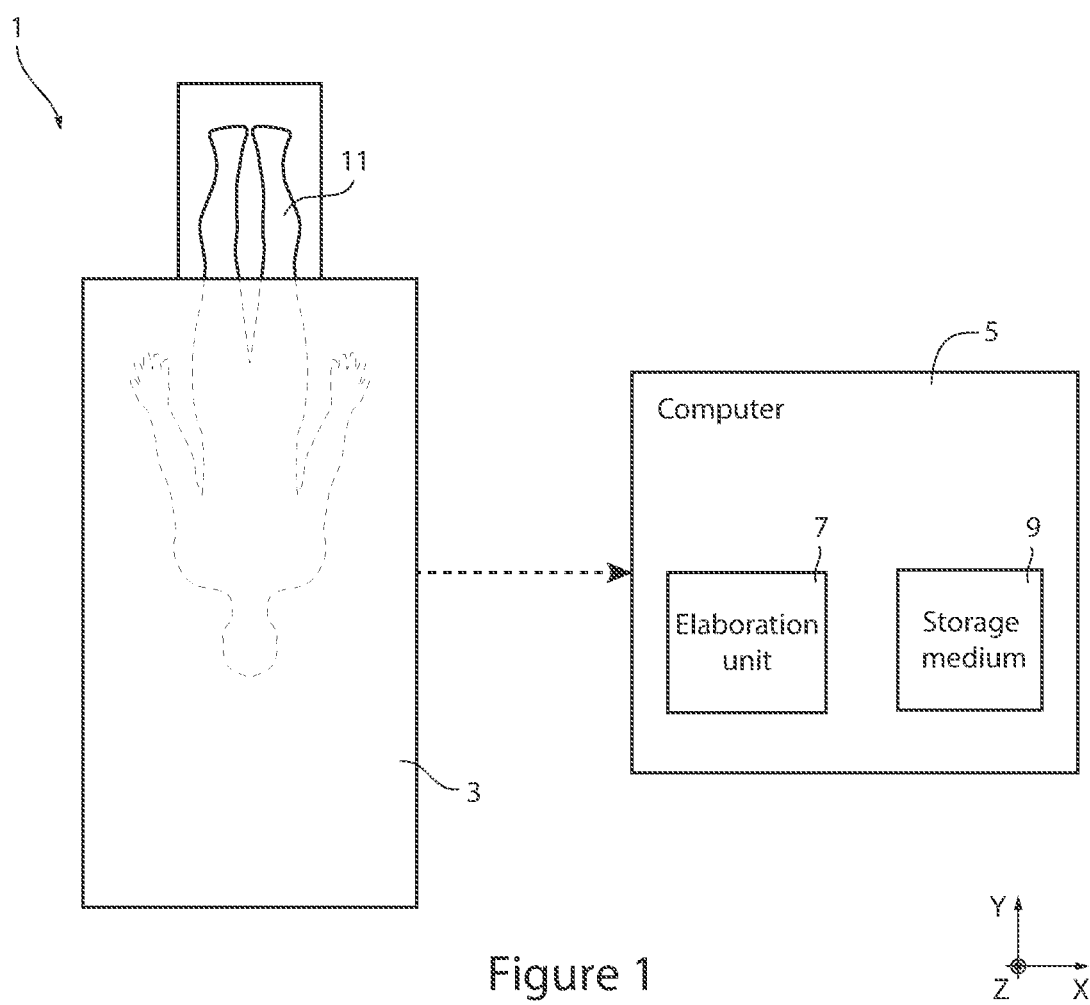
FIG. 1 schematically shows a medical equipment, according to an embodiment of the present invention.

FIG. 1 shows, in a triaxial Cartesian reference system defined by axis X, Y and Z, a medical equipment 1 comprising a medical apparatus 3 and a computer 5, operatively coupled between them. In particular, the medical apparatus 3 is a Computed Tomography (CT) apparatus (or machine), referred to in the following as CT apparatus 3.

For example, the medical apparatus 3 and the computer 5 are electrically coupled between them through wired connections (not shown), or they are wirelessly coupled between them (ex., through transmitting/receiving units, not shown).

The computer 5 is, for example, a general-purpose computer, a cloud, a super computer, a personal computer, a laptop computer, a palmtop computer, a mobile device, a tablet computer, a notebook computer, a desktop computer, a workstation computer, a server, or the like. In particular, the computer 5 comprises an elaboration unit 7 (e.g., a processor, a microprocessor or a central processing unit) and a computer-readable storage medium 9 (a memory, such as a flexible disk, hard disk, magnetic tape, any other magnetic medium, a CD-ROM, DVD, any other optical medium, punch cards, paper tape, a RAM, a PROM, an EPROM, a FLASH-EEPROM), coupled between them.

Figure 2:
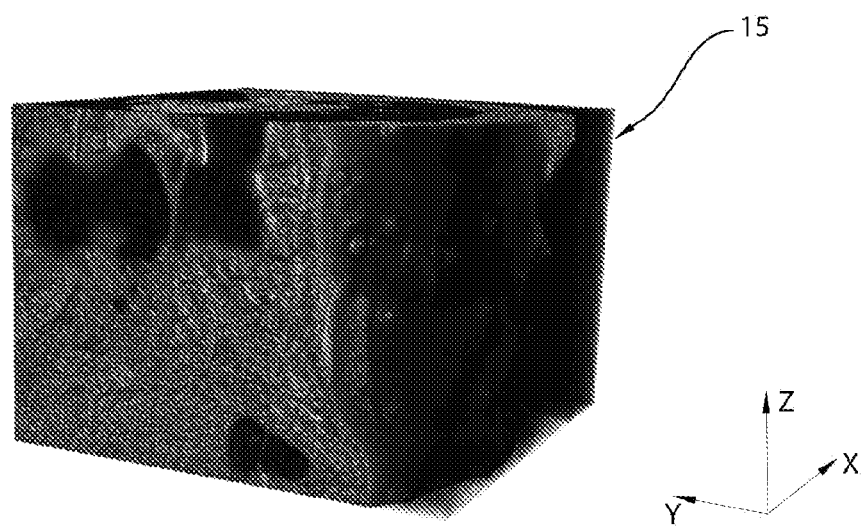
FIG. 2 shows a 3D image of a body region comprising a coronary sinus, acquired by means of the medical equipment of FIG. 1, according to an embodiment of the present invention.

With reference to FIG. 2, in use the CT apparatus 3 acquires, in a per se known way, a 3D image 15 of a body region of a patient 11. The body region is a region of interest of the body of the patient 11 and comprises an anatomical structure of interest of the patient 11 (in particular a coronary sinus shown in FIG. 7 with the reference number 100, i.e., the group of veins joined together to form a large vessel that collects blood from the heart muscle and that delivers less-oxygenated blood to the right atrium of the patient 11). More in detail, the body region comprises the coronary sinus and one or more further body tissues or organs that are adjacent, or in proximity, to the coronary sinus. Therefore, the 3D image 15 always represents the coronary sinus of the patient 11; this is achieved by appropriately programming the CT apparatus 3, in a per se known way, so that it generates and detect rays oriented in such a way to pass through said body region.

The 3D image 15, representing the body region of the patient 11, is provided as an output of the CT apparatus 3. In particular, the 3D image 15 is a first 3D matrix having first sizes (ex., having N rows, M columns and L levels, i.e., N×M×L where, for example, N=M=L). For example, the 3D image 15 is in a Digital Imaging and Communications in Medicine (DICOM) format. This format allows to store medical images as well as the patient information. Personal data is anony-mized; thus, no patient data is required for the proposed method. Moreover, the DICOM file could present the information about the coordinates of the image, for example, Image Orientation, Image Position, Slice Thickness. This is useful when the conversion from DICOM to a 3D image array is performed.

Input data, generated by the CT apparatus 3 and including the 3D image 15, are received by the computer 5. In particular, the input data are stored in the storage medium 9 and are processed by the elaboration unit 7 to obtain a 3D mask (shown in FIG. 4 with the reference number 30) of the coronary sinus of the patient 11.

Figures 3, 5:
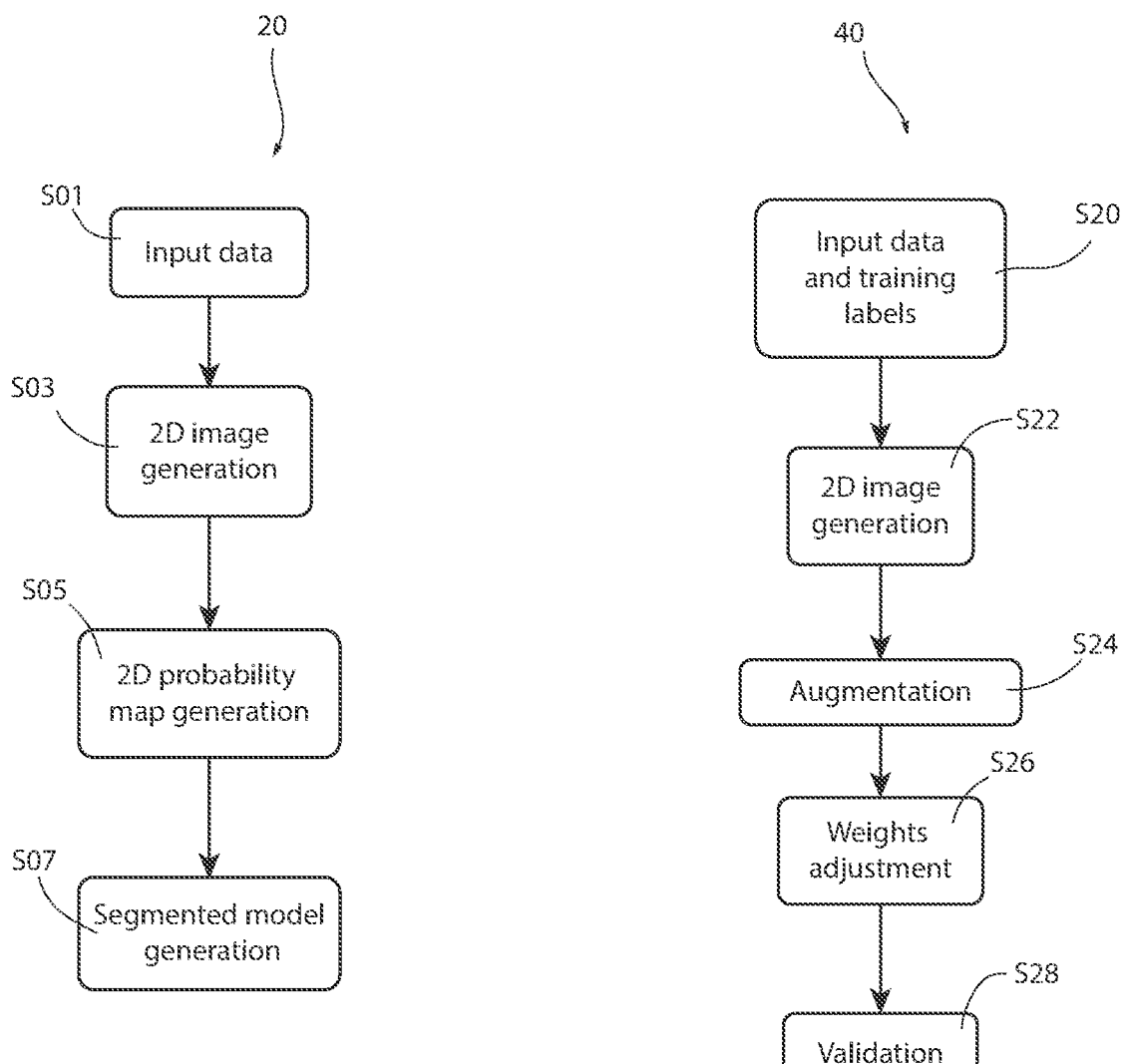
FIG. 3 is a block diagram schematically showing a coronary sinus segmentation method based on the 3D image of FIG. 2, according to an embodiment of the present invention.
FIG. 5 is a block diagram schematically showing a training method of a neural network model implemented in the coronary sinus identification method of FIG. 3, according to an embodiment of the present invention.

In use, the computer 5 (in particular, the elaboration unit 7) implements an identification (or segmentation) method 20 to generate the 3D mask 30 based on the input data (thus on the 3D image 15). In particular, FIG. 3 shows the identification method 20 according to an embodiment of the present invention.

In a step S01 of the identification method 20, the input data are acquired through the CT apparatus 3 and are received by the computer 5, as previously described.

Figure 4:
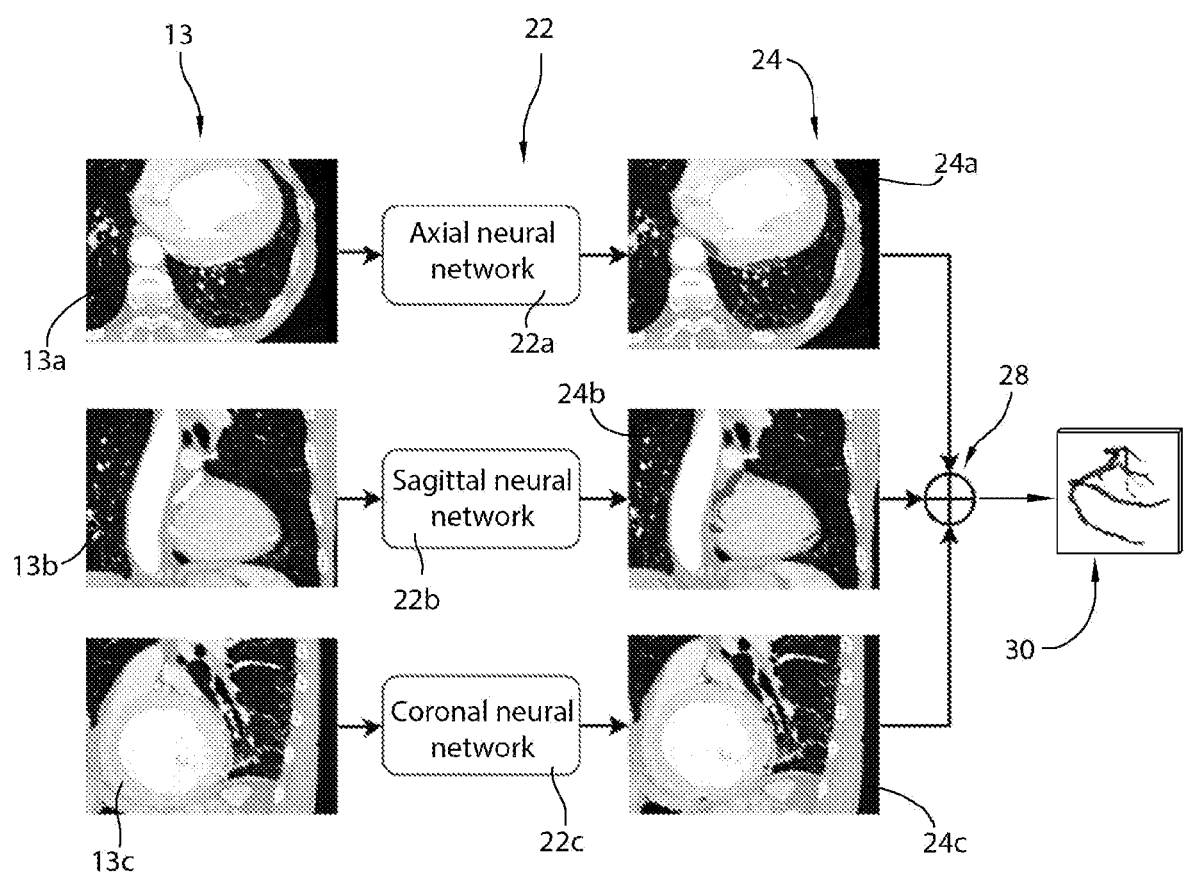
FIG. 4 is a diagram schematically showing steps of the coronary sinus identification method of FIG. 3, according to an embodiment of the present invention.

In a step S03 of the identification method 20, immediately consecutive to the step S01, the 3D image 15 comprised in the input data is pre-processed to generate a series of 2D images (shown in FIG. 4 with the reference number 13). In particular, the 3D image 15 comprises information of the body region along three scanning planes, also known as anatomical planes (here considered orthogonal with the axis X, Y and Z, although it is clear that each scanning plane could be a weighted combination of planes defined by the axis X, Y and Z). Therefore, in step S03 the 3D image 15 is decomposed into the series of 2D images 13 so that the series of 2D images 13 comprises axial images (shown in FIG. 4 with the reference number 13a, each axial image 13a being associated to a respective axial plane that is parallel to an XY plane defined by the axis X and Y), sagittal images (shown in FIG. 4 with the reference number 13b, each sagittal image 13b being associated to a respective sagittal plane that is parallel to an XZ plane defined by the axis X and Z) and coronal images (shown in FIG. 4 with the reference number 13c, each coronal image 13c being associated to a respective coronal plane that is parallel to an YZ plane defined by the axis Y and Z). In particular, each axial image 13a is a respective first 2D matrix having second sizes (e.g., N rows and L levels), each sagittal image 13b is a respective second 2D matrix having third sizes (e.g., M columns and L levels) and each coronal image 13c is a respective third 2D matrix having fourth sizes (e.g., N rows and M columns).

Optionally, in step S03 the series of 2D images 13 is further pre-processed through normalization. In particular, a standardization is applied to each 2D image 13, for example through the following formula:

$$z_{i,j} = \frac{x_{i,j} - \mu_j}{\sigma_j}$$

where, considering the j-th patient 11, $z_{i,j}$ is the i-th normalized 2D image 13, $x_{i,j}$ is the i-th input 2D image 13, $\mu_j$ is a mean value of the 3D image of j-th patient, and $\sigma_j$ is a standard deviation value of the 3D image of j-th patient. In CT images, x values are referred to Hounsfield units (HU) corresponding to the x-ray attenuation (which is different for tissues with different density).

In a step S05 of the identification method 20, immediately consecutive to the step S03, the series of 2D images 13 is iteratively processed through a first neural network model (shown in FIG. 4 with the reference number 22).

The first neural network model 22 comprises a plurality of neural networks, and in particular an axial neural network (shown in FIG. 4 with the reference number 22a) for processing the axial images 13a, a sagittal neural network (shown in FIG. 4 with the reference number 22b) for processing the sagittal images 13b, and a coronal neural network (shown in FIG. 4 with the reference number 22c) for processing the coronal images 13c. Each neural network 22a, 22b, 22c is trained, as better described in the following, to generate, based on each 2D image 13 received as input, a respective 2D probability map (shown in FIG. 4 with the reference number 24). In particular, the axial neural network 22a generates a respective axial 2D probability map 24a based on each axial image 13a, the sagittal neural network 22b generates a respective sagittal 2D probability map 24b based on each sagittal image 13b, and the coronal neural network 22c generates a respective coronal 2D probability map 24c based on each coronal image 13c. Each 2D probability map 24a, 24b, 24c is a 2D matrix having same sizes as the respective axial, sagittal or coronal image 13a, 13b, 13c: each 2D axial probability map 24a is a fourth 2D matrix having the second sizes, each 2D sagittal probability map 24b is a fifth 2D matrix having the third sizes, and each 2D coronal probability map 24c is a sixth 2D matrix having the fourth sizes. Each cell of such 2D matrix is thus associated with a respective pixel of the 2D image 13 received as input and has a respective value (comprised between, or equal to, 0 and 1) indicative of a probability that the correspondent pixel of the 2D image 13 belongs to the coronary sinus of the patient 11 (i.e., that the correspondent pixel of the 2D image 13 represents a portion of the coronary sinus).

According to an embodiment of the present invention, each neural network 22a, 22b, 22c includes two parts: a first part, an encoder, used to reduce the resolution of the input 2D image 13 in order to extract contextual information (i.e., features of the 2D images 13a, 13b, 13c); and a second part consequent to the encoder, a decoder, used to increase the resolution of the extracted contextual information in order to determine an exact location of the feature of interest (i.e., the coronary sinus of the patient 11). For example, each neural network 22a, 22b, 22c has an architecture based on Unet or Linknet. More in detail, each neural network 22a, 22b, 22c may comprise at least one convolutional layer, max-pooling layer, upsampling layer, skip-connection layer, batch-normalization layer, rectified linear layer, concatenation layer, and any other layers in any appro-priate configuration.

Alternatively, each neural network 22a, 22b, 22c presents the previously described en-coder-decoder structure, but the encoder is replaced with a convolutional neural network (CNN), for example trained on large datasets (such as ImageNet) to further improve the extraction of the contextual information. Examples of convolutional neural networks used as encoder are VGG, ResNet and Inception. The task of segmentation of some structure (or several different structures) in an image is also called semantic segmentation. For semantic segmentation, these examples of CNN are state-of-the-art techniques. As further known examples, Region-based Convolutional Neural Networks can be used for the semantic segmentation task. All architectures described above can also be called extensions of classical Convolutional Neural Networks (CNNs) as well as Fully Convolutional Networks (FCNs). Simpler versions of CNN or FCN can also be used for semantic segmentation task. The CNN may comprise convolutional, pooling, activation layers, and a fully connected layer at the end; other layers, such as a normalization layer, can also be part of CNN. FCN is similar to CNN, with the only difference that compared to CNN, FCN can accept an image of any size as input, since FCN uses 1×1 convolutional layers instead of fully connected layers.

Therefore, at step S05 each neural network 22a, 22b, 22c generates, based on the respective input 2D image 13a, 13b, 13c, one respective 2D probability map 24a, 24b, 24c at each iteration (i.e., at each time instant or time interval). Therefore, the step S05 is repeated multiple times and iterated until all the 2D images 13 have been processed and all the respective 2D probability maps 24a, 24b, 24c have been generated.

In a step S07 of the identification method 20, immediately consecutive to the step S05, the 2D probability maps 24a, 24b, 24c obtained based on all the 2D images 13 are processed to generate the 3D mask 30. In particular, the 3D mask 30 is generated by merging together all the generated 2D probability maps 24a, 24b, 24c, thus obtaining a 3D probability map (schematically shown in FIG. 4 with the reference number 28), and by saturating the 3D probability map 28 thus generating the 3D mask 30.

The 3D probability map 28 is a second 3D matrix having the first sizes (i.e., as the 3D image 15), where each cell of the 3D matrix is associated with a respective 3D pixel of the acquired 3D image 15 and has a respective value (comprised between, or equal to, 0 and 1) indicative of a probability that the correspondent 3D pixel of the 3D image 15 belongs to the coronary sinus of the patient 11 (i.e., indicative of a probability that the correspondent 3D pixel of the 3D image 15 represents a portion of the coronary sinus).

In particular, the generated 2D probability maps 24a, 24b, 24c are merged together as a weighted average ensemble so as to allow the predictions on the different types of anatomical planes to contribute in a proportional way. For example, the 3D mask 30 is generated according to the following formula:

$$Y = w_1 \cdot \sum_i Y_i + w_2 \cdot \sum_j Y_j + w_3 \cdot \sum_k Y_k$$

where Y is the 3D probability map 28, $Y_i$ is the axial image 13a and i is comprised between 0 and a total number of axial images 13a, $Y_j$ is the sagittal image 13b and j is comprised between 0 and a total number of sagittal images 13b, $Y_k$ is the coronal image 13c and k is comprised between 0 and a total number of coronal images 13c, $w_1$ is an axial weight for the axial images 13a, $w_2$ is a sagittal weight for the sagittal images 13b, and $w_3$ is a coronal weight for the coronal images 13c. Alternatively, a specific weight can be assigned to each 2D image 13. The weights $w_1$, $w_2$, $w_3$ for each neural network 22a, 22b, 22c can be set to a same value (so that each neural network 22a, 22b, 22c makes the same contribution to the 3D probability map 28), or they can be calculated by using per se known techniques, such as a random search or a grid search. Alternatively, a per se known optimization procedure (such as a linear solver or a gradient descent optimizer, e.g., XGBoost algorithm) can be used to estimate the weights $w_1$, $w_2$, $w_3$, using a unit norm weight constraint to ensure that the sum of the weights $w_1$, $w_2$, $w_3$ is unitary.

The 3D probability map 28 is then saturated to obtain the 3D mask 30. The 3D mask 30 is a segmentation map in the form of a third 3D matrix having the first sizes (i.e., as the 3D image 15 and the 3D probability map 28), where each cell of the 3D mask 30 is associated with a respective 3D pixel (also known as voxel) of the acquired 3D image 15 and has a respective binary value (0 or 1) indicative of the belonging of the considered 3D pixel of the 3D image 15 to the coronary sinus of the patient 11 (i.e., indicative of the fact that such pixel of the 3D image 15 represents or not a portion of the coronary sinus).

In particular, each cell value of the 3D probability map 28 is compared to a threshold value: if the considered 3D probability map cell value is greater than, or equal to, the threshold value, the correspondent cell value of the 3D mask 30 is set to 1; otherwise, if the considered 3D probability map cell value is lower than the threshold value, the correspondent cell value of the 3D mask 30 is set to 0. The threshold value is determined during designing and training of the first neural network model 22. In an exemplary and non-limiting case, the threshold value is comprised between 0.5 and 1.

Figure 7:
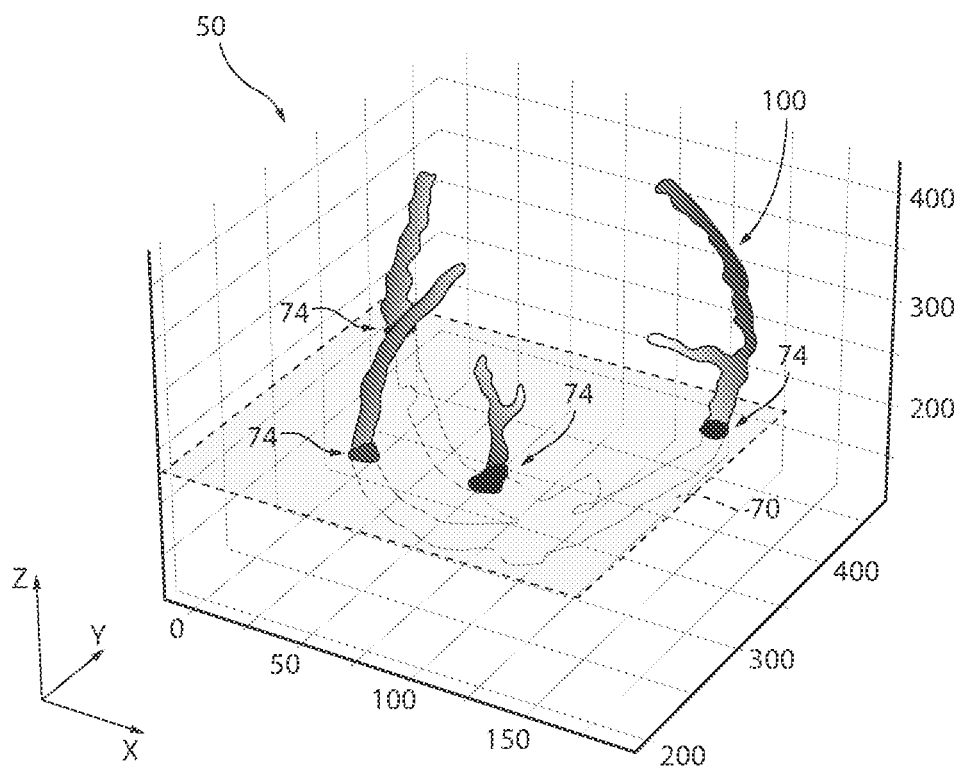
FIG. 7 shows a 3D model of the coronary sinus, obtained through the coronary sinus segmentation methods of FIGS. 3 and 6.

Therefore, the obtained 3D mask 30 is a mask that, when applied (i.e., as a Hadamard product) to the 3D image 15 used to calculate it, identifies and selects the coronary sinus while discarding any other body tissues or organs present in the 3D image 15. Consequently, by applying the 3D mask 30 to the 3D image 15, a 3D model (or representation) of the coronary sinus is obtained, extrapolated from its original environment (e.g., the adjacent tissues or organs). In details, the 3D model is a fifth 3D matrix having the first sizes and comprising a plurality of 3D pixels, each 3D pixel of the 3D model being associated to a respective 3D pixel of the 3D image 15 and having a respective value that is equal to a value of the respective 3D pixel of the 3D image 15 if the associated 3D pixel of the 3D image 15 represents the coronary sinus, or that is set to a predefined value (e.g., to 0) if the respective 3D pixel of the 3D image 15 does not represents the coronary sinus. The 3D model is also shown in FIG. 7 with the reference number 50.

With reference to FIG. 5, a training method 40 for training each neural network 22a, 22b, 22c is now described. The training method 40 can be executed before the step S01 of the identification method 20 to train the neural networks 22a, 22b, 22c, and thus is a further part of the identification method 20. The training method 40 is exemplarily described with reference to the axial neural network 22a, although it is clear that it can be analogously applied to the sagittal and coronal neural networks 22b, 22c by changing the data received as input.

In a step S20 of the training method 40, the computer 5 receives as input a training dataset comprising a plurality of training input data (and thus a respective plurality of 3D training images 15) generated by the CT apparatus 3, and a respective plurality of training labels. Each training label is associated to a respective 3D training image 15 (i.e., a respective fourth 3D matrix having the first sizes); each cell of the 3D label 30 is associated with a respective 3D pixel (also known as a voxel) of the acquired 3D image 15 and has a respective binary value (1 or 0) indicative of the belonging or not of the considered 3D pixel of the 3D image 15 to the coronary sinus of the patient 11. The training labels are provided by an operator (such as a physician skilled in segmenting the 3D training images 15 and in identifying the coronary sinus), who segments each 3D training image 15 through visual inspection.

In a step S22 of the training method 40, immediately consecutive to the step S20, each 3D training image 15 of the training dataset is pre-processed to generate a respective series of 2D training images 13, as previously described with reference to step S03 of the identification method 20. For each series of 2D training images 13, the training label of the 3D training image 15 generating said series is associated with each 2D training image 13 of the series. Since the training method 40 is described with reference to the axial neural network 22a, only the axial training images 13a generated from the training dataset are considered in the following.

In a step S24 (optional) of the training method 40, immediately consecutive to the step S22, the axial training images 13a from the plurality of series of 2D training images 13 are processed through data augmentation to obtain augmented axial training images 13a (i.e., an higher number of axial training images 13a). Data augmentation is a technique used to increase the diversity of the training dataset at input of a neural network, by applying random transformations to such training dataset. Several random transformations may be applied to each axial training image 13a, such as zoom, rotation, vertical shift, horizontal shift, elastic transformations, contrast, brightness. Parameters of the random transformation are selected empirically so that, after the transformations, the realism of the augmented axial training images 13a is preserved.

In a step S26 of the training method 40, immediately consecutive to the step S24, each one of the axial training images 13a (augmented or not) from the plurality of series of 2D training images 13 is set as input to the axial neural network 22a. The axial neural network 22a is thus trained, based on the axial training images 13a and by means of an optimization algorithm, in order to create an optimized set of weights of the axial neural network 22a. The optimization algorithm is an algorithm that determines how the weights of a neural network are calculated and updated at each stage of training. Examples of known optimization algorithms are Adam, Adagrad and Adadelta. Tuning parameters of the axial neural network 22a and/or of the optimization algorithm may be adjusted empirically or by means of a random or grid search. The optimized set of weights of the axial neural network 22a is therefore found by means of the optimization algorithm while the axial neural network 22a iteratively processes the axial training images 13a generated from the training dataset. When the training is completed, the optimized set of weights of the axial neural network 22a is saved in a file (e.g., stored in the storage medium 9) for further initialization of the axial neural network 22a. In addition to the optimization algorithm, other hyper-parameters useful for the training are, for example (since all parameters depend on the task and can be adjusted either empirically or through grid search):
batch size, usually vary from 2 to 32, e.g. is equal to 16;
learning rate, e.g. equal to $5e^{-5}$; in details, there is a scheduler for the learning rate that determines its behaviour (if a particular criteria is met, the learning rate is decreased according to a specific rule), e.g. https://pytorch.org/docs/stable/optim.html#torch.optim.lr_scheduler. Re-duceLROnPlateau;
number of epochs, e.g. about 70 although adjusted empirically and depending on the loss function value (if it does not change for a certain period, then the training is stopped to prevent over-fitting);
loss function (function that impacts the weights adjustment), in details dice loss can be used.

In a step S28 (optional) of the training method 40, immediately consecutive to the step S26, a validation of the axial neural network 22a with the optimized set of weights is performed. In particular, the axial neural network 22a is tested by providing to it as an input a testing dataset, analogous to the training dataset but based on data acquired from patients different from the ones of the training dataset. In details, the testing dataset comprises a plurality of testing input data (and thus a respective plurality of testing 3D images 15) generated by the CT apparatus 3, and a respective plurality of testing labels. The axial neural network 22a generates a respective plurality of testing axial 2D probability maps 24a from the axial testing images 13a extracted from the 3D testing images 15 of the testing dataset. A known metric (such as Sørensen-Dice coefficient, Jac-card Similarity Coefficient, or Pixel Accuracy) is applied to the testing axial 2D probability maps 24a to assess, based on the testing labels, the accuracy of detection of the axial neural network 22a. For example, if the accuracy is greater than or equal to a threshold accuracy value (e.g., ranging between about 0.7 and about 1), the axial neural network 22a having the optimized set of weights is confirmed as correctly working (i.e., is suitable for the recognition task) and it can be used for the identification method 20; otherwise, if the accuracy (or the ROC area) is lower than the threshold accuracy value, the axial neural network 22a is not confirmed as correctly working and the training method 40 is carried out again.

In addition to the above, concerning the training, a Unet model (comprises encoder and decoder parts) can be used. The encoder part of the Unet model can be replaced via a pre-trained model that was pre-trained on a large dataset, commonly available. The procedure is as follows: a CNN (e.g. resnet18, resnet50, resnet101, densenet, vgg16) is trained on the large dataset (e.g. Imagenet); then, the first part (encoder) of the Unet model is replaced with this pre-trained neural network (that replaces the first half with the architecture layers and weights acquired after this pre-training); and then the Unet is trained on the previously mentioned dataset specific for coronary sinus segmentation. The architecture of the pre-trained model is chosen either empirically or through grid search. For example, resnet50 (for sagittal and coronal neural networks) and res-net101 (for axial neural network) were chosen and trained on Imagenet dataset.

Once the training method 40 has been successfully performed for each neural network 22a, 22b, 22c, the weights $w_1$, $w_2$, $w_3$ of the weighted average ensemble are also calculated, as previously described.

Figure 6:
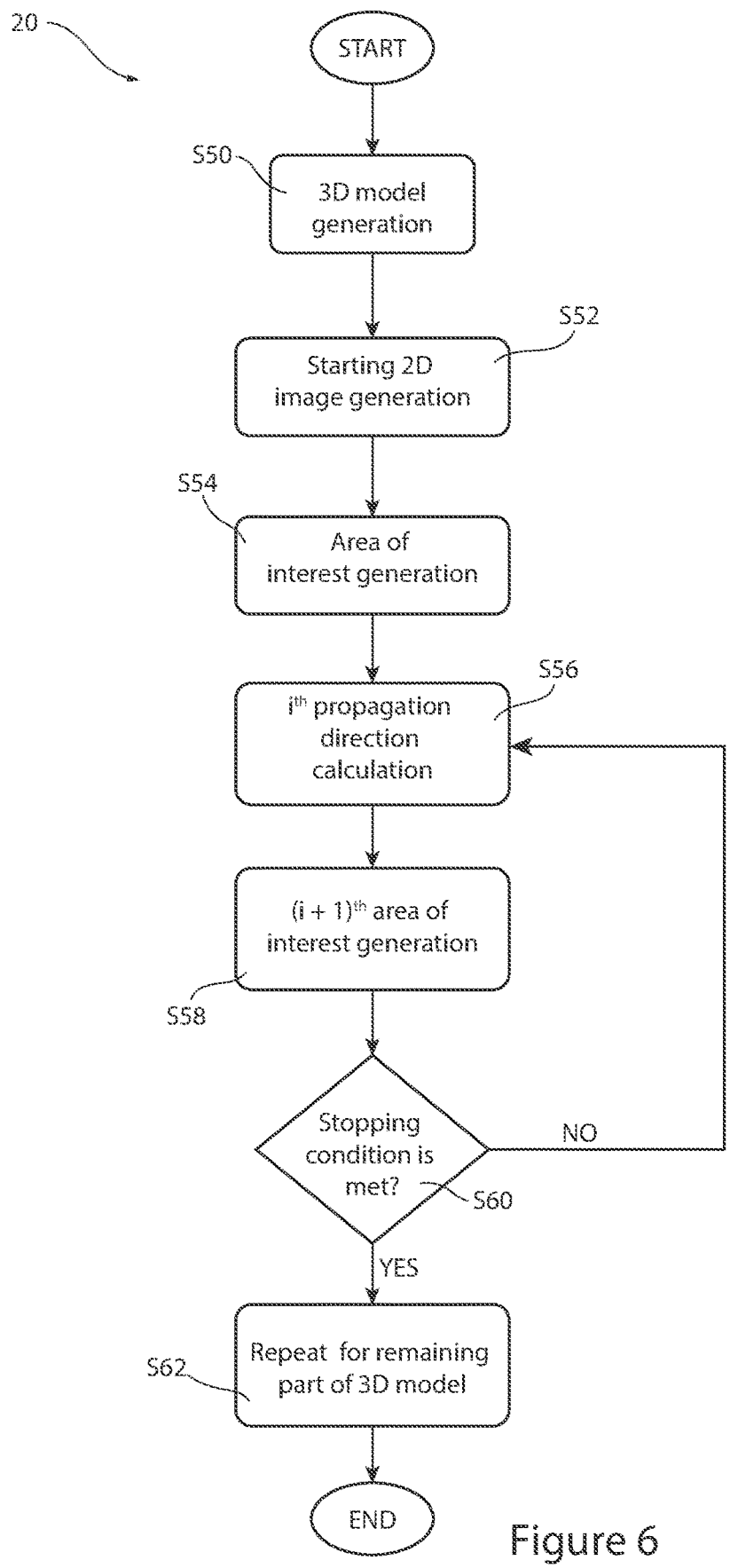
FIG. 6 is a block diagram schematically showing steps of the coronary sinus segmentation method based on the 3D image of FIG. 2, according to a different embodiment of the present invention.

FIG. 6 shows the identification method 20 according to a different embodiment of the present invention.

In particular, the identification method 20 of FIG. 6 is analogous to the identification method 20 of FIG. 3 but also comprises additional steps executed to further increase the segmentation accuracy of the coronary sinus. These additional steps are executed iteratively starting from the 3D model 50 in order to accurately reconstruct the structure of the coronary sinus in a step-by-step approach.

In a step S50 of the identification method 20 of FIG. 6, the 3D model 50 is generated as previously described with reference to FIG. 3.

In a step S52 of the identification method 20, immediately consecutive to the step S50, the 3D model 50 is processed to extract a starting 2D image 70 from the 3D model 50. The starting 2D image 70 is a 2D image of the 3D model 50 (i.e., a slice of the 3D model), for example orthogonal to one of the directions of the 3D model 50 (i.e., orthogonal to the X, Y or Z axis). As a non-limiting example, the starting 2D image 70 is considered in the following as a slice parallel to the XY plane and orthogonal to the Z axis. Preferably, the starting 2D image 70 is taken at about half of its length along the Z axis (ex., at L/2, where the 3D model 50 has N rows in the X axis, M columns in the Y axis and L levels in the Z axis): the choice of L/2 maximizes the probability of finding a portion of the coronary sinus in the starting 2D image 70.

In a step S54 of the identification method 20, immediately consecutive to the step S52, a number of portions of the coronary sinus (in particular, a number of branches of the coronary sinus) present in the starting 2D image 70 are detected and, for each branch, a respective area of interest within the starting 2D image 70 is identified. In details, the starting 2D image 70 is processed to identify if (and if yes, how many and in which positions) branches of the coronary sinus are present in the starting 2D image 70. Due to the 3D shape of the coronary sinus, each branch is shown in section in the starting 2D image 70 by means of its contour that has a circular shape (i.e., a closed polygonal shape), as it can be seen in FIG. 7 where the branch contours in the starting 2D image 70 are identified with the reference number 74.

According to an embodiment of the present invention, the branch contours 74 are identified by processing the starting 2D image 70 through a second neural network model (also called contour neural network model), better discussed in the following. In particular, the starting 2D image 70 is set as input to a first contour neural network of the second neural network model, which is trained to identify branch contours in the input 2D image (i.e., to identify the shapes of the branch contours 74 in the starting 2D image 70). Further details about the second neural network model are given in the following.

Moreover, for each detected branch contour, a respective centre (e.g., centre of mass) and extension of the branch contour are identified in step S54. In particular, for each branch contour a respective minimum enclosing circle is calculated (i.e., the smallest circle that completely encloses the branch contour 74), and both the centre and the radius of the minimum enclosing circle are identified. These centre and radius correspond respectively to the centre and the extension of the branch contour.

If no branch contour is detected, a different starting 2D image 70 is chosen (i.e., steps S52 and S54 are repeated). If at least one branch contour is detected, the respective area of interest is identified in the starting 2D image 70. In details, each area of interest is a 2D portion of the starting 2D image 70, which includes the branch contour, is centred in the centre of the branch contour and that has dimensions (e.g., $n_j \times m_j$, with $n_j < N$ and $m_j < M$ and for example $n_j = m_j$) that are correlated to the extension of the respective branch contour, and in particular is larger than the branch contour 74. In this way, the area of interest completely represents the branch contour, and no portions of the latter are excluded from it. As an example, the dimensions of the area of interest are proportional to the extension of the branch contour and, for instance, $n_j = m_j = k \cdot R_1$ where $R_1$ is the extension of the branch contour (i.e., the radius of the respective minimum enclosing circle) and k is a multiplication coefficient (e.g., k=2.5).

Therefore, at the end of step S54, both the branch contours (with the respective centres) and the respective areas of interest are determined.

Figure 8:
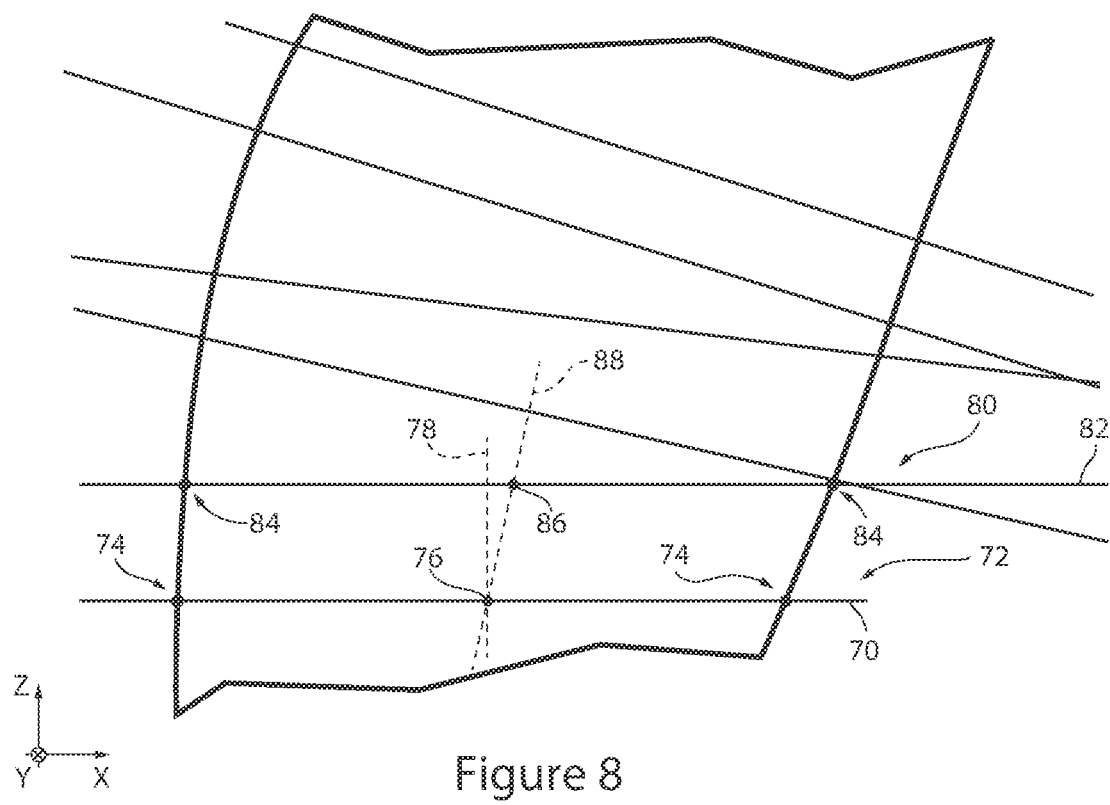
FIG. 8 graphically shows an algorithm implemented in the coronary sinus segmentation method of FIG. 6, according to a different embodiment of the present invention.

FIG. 8 shows, in the XZ plane orthogonal to the starting 2D image 70, an exemplary area of interest 72, the respective branch contour 74 and the centre 76 of the branch contour 74. In the following, the description relates for simplicity to the case of only one area of interest 72 in the starting 2D image 70, although it is evident that it analogously applies to each area of interest 72 when a plurality of areas of interest 72 are identified in the starting 2D image 70.

In a step S56 of the identification method 20, immediately consecutive to the step S54, an $i^{th}$ propagation direction 78 is calculated for the area of interest 72 (also named $i^{th}$ area of interest 72). The $i^{th}$ propagation direction 78 is, at the first iteration (i=1) of the identification method 20, a direction that is orthogonal to the $i^{th}$ area of interest 72 and that passes from its centre 76 (in the following, named $i^{th}$ centre 76); moreover, the $i^{th}$ propagation direction 78 is chosen to have a predefined versus (e.g., upwards along the Z axis), thus starting a first global cycle of coronary sinus segmentation. A different way of determining the $i^{th}$ propagation direction 78 is described in the following for the following iterations (i>1).

In a step S58 of the identification method 20, immediately consecutive to the step S56, an $(i+1)^{th}$ area of interest 80 is determined. In particular, the $(i+1)^{th}$ area of interest 80 extends orthog-onally to the $i^{th}$ propagation direction 78, is centred with the $i^{th}$ centre 76 along the $i^{th}$ propagation direction 78 and, for example, is spaced with respect to the $i^{th}$ area of interest 72 of a predefined distance (e.g., determined empirically and, for example, equal to 2 pixels) measured along the $i^{th}$ propagation direction 78 between the centres of the $i^{th}$ and $(i+1)^{th}$ areas of interest. In other words, the $(i+1)^{th}$ area of interest 80 is selected in a further 2D image (slice) of the 3D model 50 that is perpendicular to the $i^{th}$ propagation direction 78 and that is indicated with the reference number 82 in FIG. 8. Moreover, the $(i+1)^{th}$ area of interest 80 has dimensions (e.g., $n_2 \times m_2$, with $n_2 < N$ and $m_2 < M$ and for example $n_2 = m_2$) that are correlated to the dimensions of the $i^{th}$ area of interest 72, and in particular is larger than the $i^{th}$ area of interest 72. As an example, the dimensions of the $(i+1)^{th}$ area of interest 80 are proportional to the respective dimensions of the $i^{th}$ area of interest 72 and, for instance, $n_2 = k \cdot n_j$ and $m_2 = k \cdot m_j$ (e.g., k=2.5).

Moreover, in step S58, a number of branch contours are detected in the $(i+1)^{th}$ area of interest 80.

According to the previously mentioned embodiment of the present invention, the branch contours in the $(i+1)^{th}$ area of interest 80 are identified by processing the $(i+1)^{th}$ area of interest 80 through the second neural network model.

In particular, the second neural network model comprises a plurality of contour neural networks (e.g., CNN, where one of them is the previously mentioned first contour neural network), each being designed to receive as input a respective 2D image having specific sizes (different from the sizes of the 2D images inputted to the other contour neural networks) and to identify branch contours in such 2D image. In fact, since the vein diameter can vary significantly, the area of search of the second neural network model should vary accordingly (e.g., from 2 to 512 pixels); it is very difficult to come up with a unique neural network architecture that provides equally accurate branch contour segmentation for such a huge variation in dimension of the branch contours, so several neural networks have been used here, each of which is responsible for an input of a particular width range. In particular, each neural network has a particular "neural network input size", i.e. it cannot take any other shapes as an input. If the size of the $(i+1)^{th}$ area of interest 80 does not correspond to the input size of one of the contour neural network, the $(i+1)^{th}$ area of interest 80 is resized to the closest input shape accepted by one of the contour neural network. This is via known interpolation methods (e.g., https://docs.opencv.org/3.4/da/d54/group_imgproc_transform.html#ga5bb5a1fea74ea38e1a5445ca803ff121, for example through bilinear interpolation). As a non-limiting example, the second neural network model comprises four contour neural networks: the first contour neural network receives as input 2D images with first input sizes (e.g., 352 pixels, for $(i+1)^{th}$ areas of interest 80 with sizes ranging from, for example, 160 to 512 pixels); a second contour neural network receives as input 2D images with second input sizes (e.g., 128 pixels, for $(i+1)^{th}$ areas of interest 80 with sizes ranging from, for example, 96 to 159 pixels); a third contour neural network receives as input 2D images with third input sizes (e.g., 64 pixels, for $(i+1)^{th}$ areas of interest 80 with sizes ranging from, for example, 48 to 95 pixels); and a fourth contour neural network receives as input 2D images with fourth input sizes (e.g., 32 pixels, for $(i+1)^{th}$ areas of interest 80 with sizes ranging from, for example, 2 to 47 pixels). The architecture of each contour neural network is analogous to the neural networks previously described (e.g., 22a, 22b and 22c) and will not be further discussed. Concerning the training of the second neural network model, further details are given in the following.

Therefore, the $(i+1)^{th}$ area of interest 80 is resized (if necessary) and is taken as input by the corresponding contour neural network that, by processing it, outputs a respective 2D probability map where each pixel is indicative of the probability that this pixel belongs to the coronary sinus. In details, if the $(i+1)^{th}$ area of interest 80 is resized, also the correspondent 2D probability map is resized to have same sizes of the initial $(i+1)^{th}$ area of interest 80. The 2D probability map is then processed so that a correspondent 2D mask of the branches of the coronary sinus in the $(i+1)^{th}$ area of interest 80 is generated. This is done analogously to what described before, i.e. the values of the 2D probability map are compared with a threshold value (comprised between 0 and 1 and, for example, between 0.5 and 1) and each pixel of the 2D probability map having a value that is greater than or equal to the threshold value is assigned to 1, otherwise to 0. The output of the second neural network model is thus the 2D mask representing the branch contours of the coronary sinus.

Generally, the same vein branch of the coronary sinus that is present in the $i^{th}$ area of interest 72 will be also present in the $(i+1)^{th}$ area of interest 80. Nonetheless, the vein branch of the coronary sinus that is present in the $i^{th}$ area of interest 72 could be absent in the $(i+1)^{th}$ area of interest 80 if this vein branch ended between the $i^{th}$ and the $(i+1)^{th}$ area of interest 72, 80; another possibility is that the vein branch in the $i^{th}$ area of interest 72 splits in two (or more) vein branches between the $i^{th}$ and the $(i+1)^{th}$ area of interest 72, 80 so that a plurality of branch contours are detected in the $(i+1)^{th}$ area of interest 80.

Moreover, for each detected branch contour in the $(i+1)^{th}$ area of interest 80 (exemplarily one in FIG. 8 and indicated with the reference number 84), a respective centre and extension of the branch contour 84 are identified in step S58 analogously to what previously described. In FIG. 8, the centre (in the following, also called $(i+1)^{th}$ centre) of the branch contour 84 is indicated with the reference number 86.

Therefore, at the end of step S58, both the $(i+1)^{th}$ area of interest and the respective branch contours (with the respective centres) are determined.

In a step S60 of the identification method 20, immediately consecutive to the step S58, a stopping condition is verified. In particular, the stopping condition is verified when no branch contours are detected in any of the $(i+1)^{th}$ area of interest 80 at iteration i. In other words, if no coronary sinus contours are detected for a certain vein branch (e.g., for the $(i+1)^{th}$ area of interest 80) it means that this end of the vein branch has been completely segmented (i.e., a local cycle ends); moreover, if all the ends of the veins in the first global cycle are completely segmented, the first global cycle ends. If the stopping condition is met and the first global cycle has ended, the identification method 20 proceeds to a step S62, otherwise it returns to the step S56 with a new iteration.

In details, if the stopping condition is not met steps S56-S60 are repeated for iteration i+1, i.e. a new propagation direction ($(i+1)^{th}$ propagation direction) is calculated, a new area of interest ($(i+2)^{th}$ area of interest) is generated and the correspondent branch contours are detected.

At iterations i>1 and in a default condition, the propagation direction is determined as the direction connecting the last two centres of the areas of interest that were detected. In other words, considering exemplarily i=2, the $2^{nd}$ propagation direction (indicated in FIG. 8 with the reference number 88) is the direction connecting the $i^{th}$ centre 76 and the $(i+1)^{th}$ centre 86.

More in details, according to an embodiment, the $i^{th}$ propagation direction is calculated for i>1 according to the following formula:

$$P[i] = P[i-1] + S \cdot \frac{P[i-1] - P[i-2]}{\|P[i-1] - P[i-2]\|}$$

where P[n] is the centre of the area of interest at iteration n and S is a multiplication coefficient (e.g., equal to the predefined distance between the $(i+1)^{th}$ area of interest 80 and the $i^{th}$ area of interest 72 and, for example, equal to 2 pixels).

According to a different embodiment, the $i^{th}$ propagation direction is calculated for i>1 according to the following formula:

$$P[i] = P[i-1] + S \cdot \frac{P[i-1] - F(P)}{\|P[i-1] - F(P)\|}, \text{ with, e.g., } F(P) = \frac{\sum_{j=-3}^{-1} P[-j]}{3}$$

where F(P) is a filter function.

Nonetheless, if a perpendicular vein condition (shown in FIGS. 9A and 9B) is detected, the $i^{th}$ propagation direction is determined differently than what previously discussed. The perpendicular vein condition is verified when the vein branch splits in two vein branches that extend in prosecution between each other, almost along a same direction (i.e., when the vein branch bifur-cates in two vein branches substantially forming a T-shaped connection).

Figure 9A:
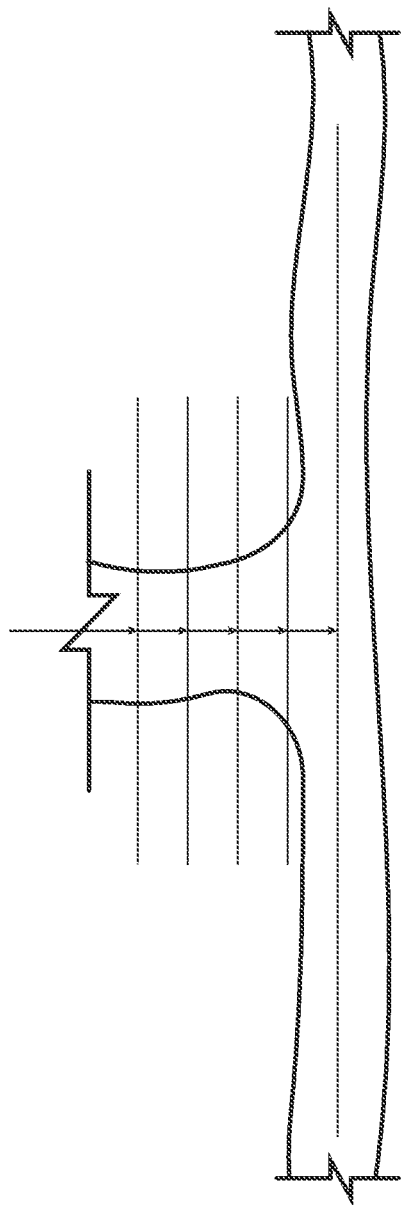
FIGS. 9A and 9B show a portion of the coronary sinus in a perpendicular vein condition.

The perpendicular vein condition is detected when the extension of a vein branch, when compared with the respective area of interest, is greater than a threshold; in fact, since the area of interest is determined based on the extension of the vein branch at the previous iteration, having at the current iteration a vein branch that is too big with respect to what can be expected means that the contour seen at the current iteration is actually indicative of the joining section of two vein branches, as shown in FIG. 9A. More in details, the perpendicular vein condition is detected when, at a current iteration, a ratio between the number of boundary pixels indicative of branch contour and the overall number of boundary pixels (i.e., pixels at the boundaries of the current area of interest) is greater than a threshold value (e.g., when $G_{cont}/G_{tot}>G_{thres}$, with for example $G_{thres}=0.1$).

Figure 9B:
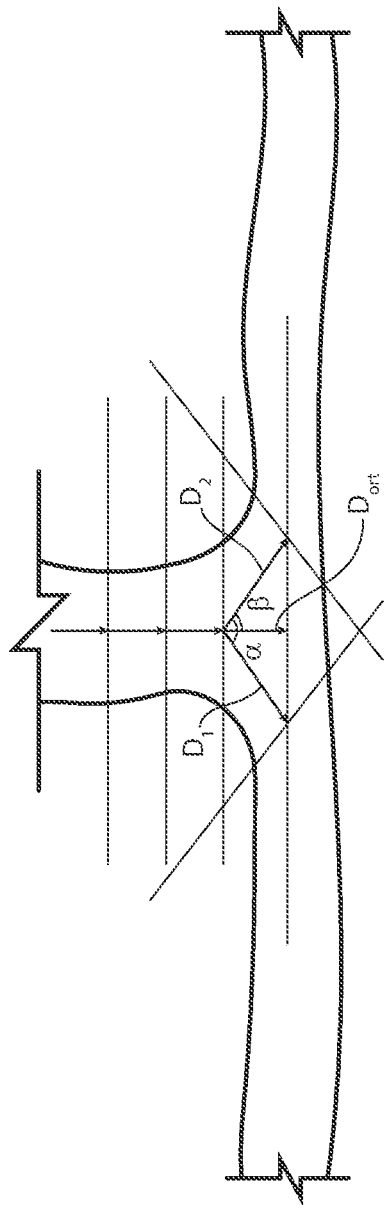

Therefore, if by using the default approach for determining the propagation direction the perpendicular vein condition is verified, the steps of calculating the propagation direction and the consecutive area of interest are repeated by using the following approach: instead of a single propagation direction, a first and a second propagation directions are used at the current iteration for determining respective areas of interest (that are indicative of respective vein branches), as shown in FIG. 9B. In particular, the first and a second propagation directions $D_1$ and $D_2$ define default angles $\alpha$ and $\beta$(opposite to each other) with respect to a direction $D_{ort}$ orthogonal to the current area of interest. As an example, the angles $\alpha$ and $\beta$ range from about ±30° to about ±60°, and for example are equal to about ±45°.

If, on the other hand, the stopping condition is met (step S62, immediately consecutive to step S60), steps S54-S60 are repeated by choosing the $i^{th}$ propagation direction 78 at the first iteration (i=1) as the opposite direction with respect to the previously chosen $i^{th}$ propagation direction 78 at the first iteration (i=1). For example, if the $1^{st}$ propagation direction 78 previously chosen pointed upwards along the Z axis, the currently chosen $1^{st}$ propagation direction 78 points down-wards along the Z axis. In this way, a second global cycle of coronary sinus segmentation is carried out to segment the coronary sinus below the starting 2D image 70, thus achieving a complete segmentation of the coronary sinus (i.e., on both sides of the starting 2D image 70).

After step S62 the identification method 20 ends.

The training method for the second neural network model is analogous to the training method 40 of FIG. 5, and thus will not be further described. Optionally, the only difference is that the generation of the 2D images is done by creating patches starting from the 3D model 50 and also by generating random 2D patches of different shapes and positions, in a per se known way.

From what has been described and illustrated previously, the advantages of the present invention are evident.

The identification method 20 allows to implement an automatic recognition of the coronary sinus of the patient 11. This leads to a reduction of time required for such recognition, and to the fact that the identification method 20 can be executed also by operators not specifically trained in segmenting medical images acquired through the CT apparatus 3 (i.e., by operators other than highly trained physicians).

The identification method 20, being automatically performed by the computer 5, prevents from human errors, inexperience or negligence that can cause the medical images to be wrongly segmented, with beneficial effects on the health of the patients 11 that can now be correctly diag-nosed and thus suitably medically treated.

The accuracy of recognition of the coronary sinus ranges from about 0.65 to about 1, which is comparable with the accuracy of manual segmentation through visual inspection.

Furthermore, the medical images can present artifacts such as noise and motion, and the shape of the coronary sinus can vary from patient to patient, as well as its prominence. The identification method 20 is robust to noise and motion and takes into account spatial information, due to the presence of the neural networks 22a, 22b, 22c, and therefore is a suitable method for coronary sinus recognition and segmentation.

Finally, it is clear that modifications and variations may be made to what has been described and illustrated herein, without thereby departing from the scope of the present invention, as defined in the annexed claims.

For example, instead of using a 2D approach for the segmentation, a 3D approach can be chosen. In other words, the segmentation by neural networks can be done through 3D input data instead of 2D ones. In this case, the architecture is changed from 2D CNN to 3D CNN (e.g. unet3D https://arxiv.org/pdf/1606.06650.pdf; the architecture is the same except that all layers are changed to 3D), the input values for the neural networks are 3D images and the corresponding outputs are 3D prediction masks.

For the identification method of FIG. 3, the prediction can be done either on the whole 3D image (e.g., 512*512*N image) or on overlapped 3D patches. From every input image, over-lapping cubes with a specified size and step (e.g., cubes 64*64*64 and step size between these over-lapped cubes equal to 32 pixels) can be selected and the resulted prediction is the mask comprising mean or maximum values of the predictions on the cubes (e.g., if several cubes share the same voxel, the output value of the 3D mask in that voxel is the mean or the maximum value of all the predictions).

For the identification method of FIG. 6, same discussion applies as already described: 3D cubes of interest are extracted (e.g., extracting cubes that each comprises the correspondent 2D area of interest, or extracting rotated cubes whose z-axes are parallel to the propagation directions) and used as inputs to the second neural network model outputting a 3D mask, the propagation directions are determined based on this prediction and the steps are repeated.

The invention claimed is:

1. Method for identifying a coronary sinus of a patient, comprising the steps of:
   acquiring, through a 3D image acquisition medical apparatus operatively coupled to a computer, a 3D image of a body region of the patient, the body region comprising the coronary sinus;
   receiving, by the computer, the 3D image;
   extracting, by the computer, 2D axial images of the 3D image taken along respective axial planes, 2D sagittal images of the 3D image taken along respective sagittal planes orthogonal to the axial planes, and 2D coronal images of the 3D image taken along respective coronal planes orthogonal to the axial planes and the sagittal planes;
   processing, by the computer, each 2D axial image through an axial neural network to generate a respective 2D axial probability map, each 2D sagittal image through a sagittal neural network to generate a respective 2D sagittal probability map, and each 2D coronal image through a coronal neural network to generate a respective 2D coronal probability map,
   wherein each 2D axial probability map comprises a plurality of cells, each being associated to a respective pixel of the respective 2D axial image and having a respective value indicative of a respective probability that said respective pixel of the respective 2D axial image represents the coronary sinus of the patient, wherein each 2D sagittal probability map comprises a plurality of cells, each being associated to a respective pixel of the respective 2D sagittal image and having a respective value indicative of a respective probability that said respective pixel of the respective 2D sagittal image represents the coronary sinus of the patient, and wherein each 2D coronal probability map comprises a plurality of cells, each being associated to a respective pixel of the respective 2D coronal image and having a respective value indicative of a respective probability that said respective pixel of the respective 2D coronal image represents the coronary sinus of the patient;

merging together, by the computer, the 2D axial probability maps, the 2D sagittal probability maps and the 2D coronal probability maps to obtain a 3D probability map comprising a plurality of cells, each being associated to a respective pixel of the 3D image and having a respective value indicative of a respective probability that said respective pixel of the 3D image represents the coronary sinus of the patient;

generating, by the computer, a 3D mask of the coronary sinus of the patient based on the 3D probability map, the 3D mask comprising a plurality of cells, each being associated to a respective pixel of the 3D image and having a respective binary value indicative of the fact that said respective pixel of the 3D image represents the coronary sinus of the patient;

applying the 3D mask to the 3D image to generate a 3D model of the coronary sinus of the patient, the 3D model comprising a plurality of pixels, each being associated to a respective pixel of the 3D image and having a respective value:

equal to a value of the respective pixel of the 3D image, if the associated pixel of the 3D image represents the coronary sinus; or set to a predefined value, if the respective pixel of the 3D image does not represent the coronary sinus;

extracting a starting 2D image from the 3D model;

verifying the presence in the starting 2D image of one or more branch contours, each being indicative of a respective vein branch of the coronary sinus; and for each branch contour detected in the starting 2D image:
a) determining a first area of interest of the starting 2D image, comprising the branch contour;
b) calculating a first propagation direction orthogonal to the first area of interest and passing through a centre of the branch contour;
c) determining a further area of interest in a further 2D image of the 3D model, orthogonal to the first propagation direction;
d) verifying the presence in the further area of interest of one or more branch contours;
e) for each branch contour detected at step d), calculating an updated propagation direction passing through a centre of the considered branch contour, and repeating the steps c)-e) with the updated propagation direction until a stopping condition is met.

2. Method according to claim 1, wherein the 3D image is a first 3D matrix having first sizes, wherein each 2D axial image is a respective first 2D matrix having second sizes, each 2D sagittal image is a respective second 2D matrix having third sizes and each 2D coronal image is a respective third 2D matrix having fourth sizes, wherein each 2D axial probability map is a fourth 2D matrix having the second sizes, each 2D sagittal probability map is a fifth 2D matrix having the third sizes, and each 2D coronal probability map is a sixth 2D matrix having the fourth sizes, wherein the 3D probability map is a second 3D matrix having the first sizes, and wherein the 3D mask is a third 3D matrix having the first sizes.

3. Method according to claim 1, wherein processing each 2D axial image comprises using an axial encoding structure for receiving each 2D axial image and for generating respective axial features, and using an axial decoding structure for receiving the respective axial features and for generating the respective 2D axial probability map, wherein processing each 2D sagittal image comprises using a sagittal encoding structure for receiving each 2D sagittal image and for generating respective sagittal features, and using a sagittal decoding structure for receiving the respective sagittal features and for generating the respective 2D sagittal probability map, wherein processing each 2D coronal image comprises using a coronal encoding structure for receiving each 2D coronal image and for generating respective coronal features, and using a coronal decoding structure for receiving the respective coronal features and for generating the respective 2D coronal probability map.

4. Method according to claim 1, wherein the step of extracting the 2D axial images, the 2D sagittal images and the 2D coronal images further comprises normalizing the 2D axial images, the 2D sagittal images and the 2D coronal images through standardization.

5. Method according to claim 1, wherein the step of merging together the 2D axial probability maps, the 2D sagittal probability maps and the 2D coronal probability maps comprises calculating the 3D probability map as a weighted average ensemble of the 2D axial probability maps, the 2D sagittal probability maps and the 2D coronal probability maps.

6. Method according to claim 1, wherein the step of generating the 3D mask comprises comparing the respective value of each cell of the 3D probability map with a threshold probability value and, based on such comparison, setting the respective binary value of the correspondent cell of the 3D mask.

7. Method according to claim 2, further comprising the steps of:

acquiring, through the 3D image acquisition medical apparatus, 3D training images of the body region of the patient, each 3D training image being a respective fourth 3D matrix having the first sizes;

receiving, by the computer, the 3D training images;

for each 3D training image, extracting, by the computer, 2D training axial images of the 3D training image taken along the axial planes, 2D training sagittal images of the 3D training image taken along the sagittal planes, and 2D training coronal images of the 3D training image taken along the coronal planes, wherein each 2D training axial image is a respective seventh 2D matrix having the second sizes, each 2D training sagittal image is a respective eighth 2D matrix having the third sizes and each 2D training coronal image is a respective ninth 2D matrix having the fourth sizes; and supervised training, by the computer, the axial neural network based on the 2D training axial images extracted from the 3D training images, the sagittal neural network based on the 2D training sagittal images extracted from the 3D training images, and the coronal neural network based on the 2D training coronal images extracted from the 3D training images.

8. Method according to claim 7, wherein the step of training the axial neural network, the sagittal neural network and the coronal neural network comprises using an optimization algorithm.

9. Method according to claim 7, further comprising applying data augmentation techniques to the 2D training axial images, the 2D training sagittal images and the 2D training coronal images.

10. Method according to claim 7, wherein the step of extracting the 2D training axial images, the 2D training sagittal images and the 2D training coronal images further comprises normalizing the 2D training axial images, the 2D training sagittal images and the 2D training coronal images through standardization.

11. Method according to claim 1, wherein the 3D image acquisition medical apparatus is a Computed Tomography, CT, machine.

12. Method according to claim 1, wherein the 3D model is obtained as an Hadamard product of the 3D image and the 3D mask.

13. Method according to claim 1, wherein, in a default condition, the updated propagation direction connects the centre of the considered branch contour detected in a current iteration and a centre of branch contour detected in an immediately precedent iteration, said branch contours being 2D sections of a same vein branch of the coronary sinus, and wherein, in a perpendicular vein condition in which the considered branch contour detected in the current iteration is indicative of a bifurcation of the considered vein branch of the coronary sinus, two propagation directions ($D_1$, $D_2$) symmetrical between each other with respect to a direction ($D_{ort}$) orthogonal to the branch contour detected in the immediately precedent iteration are determined, each propagation direction being ($D_1$, $D_2$) indicative of a respective bifurcated vein branch originating from the considered vein branch of the coronary sinus.

14. Method according to claim 1, wherein the stopping condition is met when, in a current iteration, no branch contours are detected in any further area of interest.

15. Method according to claim 1, wherein verifying the presence of one or more branch contours in the starting 2D image and in the further area of interest comprises processing the starting 2D image and, respectively, the further area of interest through deep learning techniques.

16. Computer comprising an elaboration unit operatively couplable to a 3D image acquisition medical apparatus and configured to implement a method for identifying a coronary sinus of a patient, according to claim 1.

17. Computer storing a computer program product having an elaboration unit operatively couplable to a 3D image acquisition medical apparatus, the computer program being designed so that, when executed, the elaboration unit becomes configured to implement a method for identifying a coronary sinus of a patient, according to claim 1.

\* \* \* \* \*